United States Patent [19]
Taniguchi et al.

[11] Patent Number: 5,643,729
[45] Date of Patent: Jul. 1, 1997

[54] METHODS FOR DIAGNOSING CANCER, PRECANCEROUS STATE, OR SUSCEPTIBILITY TO OTHER FORMS OF DISEASES BY DETECTING AN ACCELERATION OF EXON SKIPPING IN IRF-1 MRNA

[75] Inventors: Tadatsugu Taniguchi, Ibaraki; Hisashi Harada, Suita, both of Japan

[73] Assignee: Boehringer Ingelheim International GmbH, Germany

[21] Appl. No.: 393,997

[22] Filed: Feb. 24, 1995

[30] Foreign Application Priority Data

Feb. 24, 1994 [EP] European Pat. Off. .............. 94102839

[51] Int. Cl.$^6$ .............. C12Q 1/68; C12P 19/34; C07H 21/04
[52] U.S. Cl. .............. 435/6; 435/91.2; 536/24.3; 536/24.31; 536/24.33
[58] Field of Search .............. 435/91.2; 536/24.3, 536/24.31, 24.33

[56] References Cited

U.S. PATENT DOCUMENTS 5,426,181  6/1995  Lee et al. .............. 536/23.5

FOREIGN PATENT DOCUMENTS 0 571 743  12/1993  European Pat. Off. .
WO91/02817  3/1991  WIPO .
WO92/15602  9/1992  WIPO .
WO94/06818  3/1994  WIPO .

OTHER PUBLICATIONS

Boultwood et al., "Allelic Loss of IRF1 in Myelodysplasia and Acute Myeloid Leukemia: Retention of IRF1 on the 5q–Chromosome in Some Patients With the 5q–Syndrome," *Blood* 82(9):2611–2616 (1993).

Carter et al., "Genetic Lesions in Preleukemia," *Critical Rev. Oncogenesis* 3(4):339–364 (1992).

Cha et al., "Human Interferon Regulatory Factor 1: Intron–Exon Organization," *DNA and Cell Biol.* 11(8):605–611 (1992).

Chomczynski, P. and Sacchi, N., "Single–Step Method of RNA Isolation by Acid Guanidinium Thiocyanate–Phenol–Chloroform Extraction," *Analytical Biochem.* 162:156–159 (1987).

Foley et al., "Quantitation of RNA using the polymerase chain reaction," *TIG* 9(11):380–385 (1993).

Harada et al., "Absence of the Type I IFN System in EC Cells: Transcriptional Activator (IRF–1) and Repressor (IRF–2) Genes Are Developmentally Regulated," *Cell* 63:303–312 (1990).

Harada et al., "Anti–Oncogenic and Oncogenic Potentials of Interferon Regulatory Factors–1 and –2," *Science* 259:971–974 (1993).

Harada et al., "Structurally Similar but Functionally Distinct Factors, IRF–1 and IRF–2, Bind to the Same Regulatory Elements of IFN and IFN–Inducible Genes," *Cell* 58:729–739 (1989).

(List continued on next page.)

*Primary Examiner*—Stephanie W. Zitomer
*Assistant Examiner*—Jeffrey Fredman
*Attorney, Agent, or Firm*—Sterne, Kessler, Goldstein & Fox P.L.L.C.

[57] ABSTRACT

The present invention concerns a novel molecular marker useful for diagnosing hematopoietic disorders, including cancers and precancerous conditions. The invention is based on the unexpected discovery that inactivation of the IRF-1 tumor suppressor gene can occur via an altered splicing pattern of the IRF-1 primary transcript. This altered splicing pattern leads to mRNAs lacking exon 2 or exons 2 and 3. The relative amounts of full-length RNA and shortened RNA molecules are significantly different in samples obtained from patients suffering from certain cancers and precancerous conditions as compared to healthy donors.

16 Claims, 8 Drawing Sheets

OTHER PUBLICATIONS

Harada et al., "Structure and Regulation of the Human Interferon Regulatory Factor–1 (IRF–1) and IRF–2 Genes: Implications for a Gene Network in the Interferon System," Mol. Cell. Biol. 14(2):1500–1509 (1994).

Itoh et al., "Assignment of the Human Interferon Regulatory Factor–1 (IRF–1) Gene to Chromosome 5q23–q31," Genomics 10:1097–1099 (1991).

Itoh et al., "Sequence of a cDNA coding for human IRF–2," Nucl. Acids Res. 17(20):8372 (1989).

Kerim et al., "5q– Anomaly in Lymphoid Disorders," Leukemia 4(1):12–15 (1990).

Kirchhoff et al., "Interferon regulatory factor 1 (IRF–1) mediates cell growth inhibition by transactivation of downstream target genes," Nucl. Acids Res. 21(12):2881–2889 (1993).

Le Beau et al., "Clinical and Cytogenetic Correlations in 63 Patients With Therapy–Related Myelodysplastic Syndromes and Acute Nonlymphocytic Leukemia: Further Evidence for Characteristic Abnormalities of Chromosomes No. 5 and 7," J. Clin. Oncol. 4(3):325–345 (1986).

Le Beau et al., "Cytogenetic and molecular delineation of the smallest commonly deleted region of chromosome 5 in malignant myeloid diseases," PNAS USA 90:5484–5488 (1993).

Lengyel, P., "Tumor–suppressor genes: News about the interferon connection," PNAS USA 90:5893–5895 (1993).

Levine et al., "The Tumor Suppressor Genes," Annu. Rev. Biochem. 62:623–651 (1993).

Lewin, B., "Oncogenic Conversion by Regulatory Changes in Transcription Factors," Cell 64:303–312 (1991).

Makino et al., "Evaluation of Quantitative Detection of mRNA by the Reverse Transcription–Polymerase Chain Reaction," Technique 2(6):295–301 (1990).

Maruyama et al., "Sequence of a cDNA coding for human IRF–1," Nucl. Acids Res. 17(8):3292 (1989).

Matsuyama et al., "Targeted Disruption of IRF–1 or IRF–2 Results in Abnormal Type I IFN Gene Induction and Aberrent Lymphocyte Development," Cell 75:83–97 (1993).

Miyamoto et al., "Regulated Expression of a Gene Encoding a Nuclear Factor, IRF–1, That Specifically Binds to IFN–β Gene Regulatory Elements," Cell 54:903–913 (1988).

Nimer, S.D. and Golde, D.W., "The 5q– Abnormality," Blood 70(6):1705–1712 (1987).

Pedersen, B. and Jensen, I.M., "Clinical and Prognostic Implications of Chromosome 5q Deletions: 96 High Resolution Studied Patients," Leukemia 5(7):566–573 (1991).

Pedersen–Bjergaard et al., "Chromosome Aberrations and Prognostic Factors in Therapy–Related Myelodysplasia and Acute Nonlymphocytic Leukemia," Blood 76(6):1083–1091 (1990).

Ponte et al., "Evolutionary conversation in the untranslated regions of actin mRNAs: DNA sequence of a human beta–actin cDNA," Nucl. Acids Res. 12(3):1687–1696 (1984).

Sugimoto et al., "Mutations of the p53 Gene in Myelodysplastic Syndrome (MDS) and MDS–Derived Leukemia," Blood 81(11):3022–3026 (1993).

Tanaka, N. and Taniguchi, T., "Cytokine Gene Regulation: Regulatory cis–Elements and DNA Binding Factors Involved in the Interferon System," Adv. Immunol. 52:263–281 (1992).

Tanaka et al., "Age–related changes in the proportion of amyloid precursor protein mRNAs in Alzheimer's disease and other neurological disorders," Mol. Brain Res. 15:303–310 (1992).

Tanaka et al., "Recognition DNA Sequences of Interferon Regulatory Factor–1 (IRF–1) and IRF–2, Regulators of Cell Growth and the Interferon System," Mol. Cell. Biol. 13(8):4531–4538 (1993).

Van den Berghe et al., "the 5q– Anomaly," Cancer Genet. Cytogenet. 17:189–255 (1985).

Wang et al., "Quantitation of mRNA by the polymerase chain reaction," PNAS USA 86:9717–9721 (1989).

Willman et al., "Deletion of IRF–1, Mapping to Chromosome 5q31.1, in Human Leukemia and Preleukemic Myelodysplasia," Science 259:968–971 (1993).

Yamada et al., "Specific depletion of the B–cell population induced by aberrant expression of human interferon regulatory factor 1 gene in transgenic mice," PNAS USA 88:532–536 (1991).

Harada et al, (1994), "Accelerated exon skipping of IRF–1 mRNA in human myelodysplasia leukemia; a possible mechanism of tumor suppression inactivation", Oncogene 9:3313–3320.

Cha et al, (Feb. 18, 1994), "Human interferon regulatory factor 2 gene", J. Biol. Chem. 269(7):5279–5287.

METHODS FOR DIAGNOSING CANCER, PRECANCEROUS STATE, OR SUSCEPTIBILITY TO OTHER FORMS OF DISEASES BY DETECTING AN ACCELERATION OF EXON SKIPPING IN IRF-1 MRNA

FIELD OF THE INVENTION

The present invention relates to a molecular marker useful for diagnosing hematopoietic disorders, including cancers and precancerous conditions. The invention is based on the unexpected finding that inactivation of the IRF-1 tumor suppressor gene can occur via an altered splicing pattern of the IRF-1 primary transcript.

BACKGROUND OF THE INVENTION

Malignant cell transformation is a multistep process resulting from the progressive acquisition of structural alterations at multiple genetic loci which are involved in the regulation of cell growth. It has been well documented that gain-of-function mutations, found in dominantly-acting proto-oncogenes, are often accompanied by loss-of-function mutations in tumor suppressor genes in human malignant cells. Several tumor suppressor genes have been identified whose mutation or deletion appears to be critical for the development of human cancers, among them, p53, RB and WT1, whose gene products are found in nucleus and which function as regulators of gene transcription (reviewed in Kaelin et al., Cellular proteins that can interact specifically with the retinoblastoma susceptibility gene product. In Origin of human cancer: A comprehensive review, Brugge, J., Curran, T., Harlow, E., McCormik, F. eds. (Cold Spring Harbor Laboratory Press), pp.423–431 (1991); Lewin, Cell 64:303–312 (1991); Marshall, Cell 64:313–326 (1991); Weinberg, Science 254:1138–1146 (1991); Haber and Housman, Adv. Cancer Res. 59:41–68 (1992); Vogelstein and Kinzler, Cell 70:523–526 (1992); Levine, Annu. Rev. Biochem. 62:623–651 (1993)).

Two structurally related transcription factors, IRF-1 and IRF-2 were originally identified as regulators of the interferon (IFN) system (Miyamoto, et al., Cell 54:903–913 (1988); Harada et al., Cell 58:729–739 (1989); Tanaka and Taniguchi, Adv. Immunol. 52:263–281 (1992)). IRF-1 has also been identified by others in different contexts (Pine et at., Mol. Cell. Biol. 10:2448–2457 (1990); Yu-Lee et al., Mol. Cell. Biol. 10:3087–3094 (1990); Abdollahi et at., Cell Growth Differ. 2:401–407 (1991); Stark and Kerr, J. Interferon Res. 12:147–151 (1992)). IRF-1 functions as a transcriptional activator whereas IRF-2 represses the effect of IRF-1 by competing for binding to the same DNA sequence elements (IRF-Es) (Harada et al., Cell 58:729–739 (1989); Tanaka et al., Mol. Cell. Biol. 13:4531–4538 (1993)). IRF-Es can be found in both the IFN-α and IFN-β promoters, as well as in IFN-stimulated response elements (ISREs) found within the promoters of IFN-inducible genes (Friedman and Stark, Nature 314:637–639 (1985); Shirayoshi et al., Mol. Cell. Biol. 7:4542–4548 (1987); Levy et al., Genes Dev. 2:383–393 (1988)). It has been shown that IRF-1 functions as an activator for the type I IFN genes and some IFN-inducible genes (Fujita et al., Nature 337:270–272 (1989); Harada et al., Cell 63:303–312 (1990); Au et al., Nucleic Acids Res. 20:2877–2884 (1992); Pine, J. Virol. 66:4470–4478 (1992); Reis et al., EMBO J. 11:185–193 (1992); Matsuyama et al., Cell 75:83–97 (1993); Ruffner et at., Proc. Natl. Acad. Sci. USA 90:11503–11507 (1993)).

Evidence has also been provided demonstrating a role for IRF-1 as a tumor suppressor; (i) IRF-1 manifests antiproliferative activities (Yamada et al., Proc. Natl. Acad. Sci. USA 88:532–536 (1990); Kirchhoff et al., Nucleic Acids Res. 21:2881–2889 (1993); T. Tamura, M. S. L., and T. Kawakami, unpublished results), (ii) overexpression of the repressor IRF-2 in NIH 3T3 cells causes cell transformation and this cell transformation is suppressed by concomitant overexpression of the activator IRF-1 (Harada et al., Science 259:971–974 (1993)), and (iii) primary embryonic fibroblasts (EFs) with a null mutation in the IRF-1 gene (IRF-1$^{-/-}$ mice) are susceptible to transformation by an activated form of c-Ha-ras, a property also seen in the EFs from p53$^{-/-}$ mice, but not in wild type EFs. These observations collectively suggest that the loss of IRF-1 function may contribute to the development of human neoplasia.

The human IRF-1 gene has been mapped to 5q31.1 (Itoh et al., Genomics 10:1097–1099 (1991); Willman et al., Science 259:968–971 (1993); Harada et al., Mol. Cell. Biol. 14:1500–1509 (1994)). Chromosome band 5q31 was previously determined to be the most commonly deleted segment, the so-called "critical region", in human leukemia and MDS with interstitial deletions of chromosome 5q (Le Beau et at., J. Clin. Oncol. 4:325–345 (1986); Nimer and Golde, Blood 70:1705–1712 (1987); Le Beau et al., Cancer Cells 7:53–58 (1989); Pederson and Jensen, Leukemia 5:566–573 (1991)). Del(5q) is also a hallmark of a unique clinical myelodysplastic disorder with refractory anemia and abnormal megakaryocytes occurring predominantly in elderly females, known as the "5q-Syndrome" (Van den Berghe et at., Cancer Genet. Cytogenet. 17:189–256 (1985)). Hence it is believed that this chromosomal region harbors a tumor suppressor gene(s). However, in view of the variable clinical features of myeloid diseases associated with del(5q), it is possible that inactivation of such tumor suppressor gene(s) is accompanied by variable additional genetic events such as the activation of oncogenes in different types of myeloid disorders (Carter et al., Crit. Rev. Oncog. 3:339–364 (1992)).

Previously, it had been demonstrated that one or both IRF-1 alleles were deleted in each of 13 representative cases of MDS and leukemia with del(5q) or translocation of 5q31. Furthermore, inactivating gene rearrangement of one IRF-1 allele, accompanied by deletion of the residual allele, were found in a case of de novo acute leukemia (Willman et at., 1993). These observations support the idea that IRF-1 may be the critical tumor suppressor gene deleted in the del(5q); thus loss of one or both IRF-1 alleles may contribute to unrestrained cellular proliferation thereby promoting the development of human leukemia and MDS. On the other hand, both IRF-1 alleles are still retained in some MDS/leukemia patients exhibiting 5q deletion (Boultwood et al., Blood 82:2611–2616 (1993); Ice Beau et al., Proc. Natl. Acad. Sci. USA 90:5484–5488 (1993)).

SUMMARY OF THE INVENTION

The inventors have discovered that inactivation of the IRF-1 tumor suppressor gene can occur via an altered splicing pattern of the IRF-1 primary transcript. This mechanism is independent of previously described deletions or mutations of the IRF-1 gene as it occurs where such alterations are not detectable. Thus, the invention is useful as a novel molecular marker, assayed at the RNA level, which is indicative of hematopoietic disorders, including cancers and precancerous conditions.

In addition to intact IRF-1 mRNA, IRF-1 mRNA molecules lacking exon 2 (Δ2) or exons 2 and 3 (Δ23) can be detected in biological samples obtained from either healthy donors or patients suffering from certain hematopoietic disorders. The inventors have discovered that the incidence of such "exon skipping" is accelerated significantly in many of the individuals suffering from hematopoietic disorders relative to the healthy donors.

The invention involves assaying the IRF-1 mRNA level in a first biological sample, wherein the IRF-1 mRNA is selected from one or more of intact IRF-1 mRNA, Δ2 IRF-1 mRNA, or Δ23 IRF-1 mRNA, and determining whether the sample exhibits an acceleration in exon skipping. Preferably, this determination is made by comparing the IRF-1 mRNA level to an IRF-1 mRNA standard level, wherein the standard is taken from a second biological sample not exhibiting accelerated exon skipping in IRF-1 mRNA. By the invention, an acceleration of exon skipping is exhibited if the intact IRF-1 mRNA level in the first sample is lower relative to the intact IRF-1 mRNA level in the standard. More particularly, an acceleration of exon skipping is exhibited if the ratio between the intact IRF-1 mRNA level and the Δ2 IRF-1 mRNA level or the Δ23 IRF-1 mRNA level in the first sample is lower relative to the ratio in the standard.

The invention provides a diagnostic assay for a number of hematopoietic disorders including cancers and precancerous conditions.

DETAILED DESCRIPTION OF THE INVENTION

Willman et at., Science 259:968–971 (1993), reported that deletions in the IRF-1 gene consistently occurred at one or both alleles in the 13 patients tested with aberrations in chromosomal region 5q31. However, subsequent publications (Boultwood et al., Blood 82:2611–2616 (1993), and Le Beau et al., Proc. Natl. Acad. Sci. USA 90:5484–5488 (1993)) reported that both IRF-1 alleles are still retained in some MDS/leukemia patients exhibiting the 5q31 deletion. Thus, it appears that deletion of the IRF-1 gene is not always responsible for the biological characteristics of the del(5q) and the 5q-syndromes.

The invention is based on the unexpected finding that inactivation of the IRF-1 tumor suppressor gene can occur by an altered splicing pattern of the primary IRF-1 transcript. Thus, a previously unrecognized mechanism of IRF-1 inactivation plays a crucial role in certain hematopoietic disorders. Surprisingly, the present inventors have discovered that the altered splicing pattern is present in many patients suffering from hematopoietic disorders even though there are no deletions or mutations, at the chromosomal level, in the IRF-1 exon sequences or in the intron sequences known to affect splicing. Thus, the present invention provides a novel molecular marker, assayed at the RNA level, which can be used either alone or in conjunction with other known markers as an indicator of certain hematopoietic disorders, including cancers and precancerous conditions.

More particularly, the inventors have discovered that, in addition to intact IRF-1 mRNA, IRF-1 mRNA molecules lacking exon 2 (Δ2) or exons 2 and 3 (Δ23) can be detected in biological samples obtained from either healthy donors or patients suffering from certain hematopoietic disorders. However, the incidence of "exon skipping" is accelerated (i.e, increased) significantly in many of the individuals suffering from hematopoietic disorders relative to the healthy donors. By the invention, an acceleration of exon skipping in IRF-1 mRNA is indicative of a number of hematopoietic disorders including the following cancers and precancerous conditions: overt leukemia from myelodysplastic syndrome (MDS/Leu); acute myeloid leukemia (AML); and the myelodysplastic syndromes (MDS), i.e., refractory anemia (RA), refractory anemia with ringed sideroblasts (RARS), refractory anemia with excess of blasts (RAEB), RAEB in transformation (RAEBT), chronic myelomonocytic leukemia (CMML).

By "exon skipping in IRF-1 mRNA" is intended an altered splicing pattern of the IRF-1 primary transcript resulting in IRF-1 mRNA molecules lacking, either partially or fully, exon 2 ($\Delta 2$) and/or exons 2 and 3 ($\Delta 23$). This is most often associated with a decrease in intact IRF-1 mRNA and an increase in either or both of $\Delta 2$ IRF-1 mRNA and $\Delta 23$ IRF-1 mRNA. Thus, the invention involves assaying the IRF-1 mRNA level in a first biological sample, wherein the IRF-1 mRNA is selected from one or more of intact IRF-1 mRNA, $\Delta 2$ IRF-1 mRNA, or $\Delta 23$ IRF-1 mRNA and determining whether the first sample exhibits an acceleration of exon skipping in IRF-1 mRNA.

By "assaying the IRF-1 mRNA level in a first biological sample" is intended qualitatively or quantitatively measuring the IRF-1 mRNA level in a first biological sample either directly (e.g., determining or estimating the absolute mRNA copy number) or relatively (e.g., by comparing to the IRF-1 mRNA level in a second biological sample). Preferably, whether the first sample exhibits an acceleration of exon skipping in IRF-1 mRNA is determined by comparing the IRF-1 mRNA level to an IRF-1 mRNA standard level, wherein the standard is taken from a second biological sample not exhibiting accelerated exon skipping in IRF-1 mRNA. By the invention, an acceleration of exon skipping is exhibited if the intact IRF-1 mRNA level in said first sample is lower relative to the intact IRF-1 mRNA in the standard. More particularly, an acceleration of exon skipping is exhibited if the ratio between the intact IRF-1 mRNA level and the $\Delta 2$ IRF-1 mRNA level or the $\Delta 23$ IRF-1 mRNA level in the first sample is lower relative to the same ratio in the standard.

By "biological sample" is intended any biological sample obtained from an individual, cell line, tissue culture, or other source which contains IRF-1 RNA. Sources of IRF-1 mRNA include peripheral blood mononuclear cells (PBM), bone marrow cells, umbilical cord blood cells and other biopsy samples. Methods for obtaining PBM, bone marrow cells and cord blood cells are well known in the art. The "first biological sample" can be obtained from any individual, cell line, tissue culture, or other source to be assayed for the occurrence of accelerated exon skipping in IRF-1 mRNA. The "second biological sample" can be obtained from any "healthy" individual or source known not to exhibit accelerated exon skipping in IRF-1 mRNA. Examples of "healthy" individuals include humans not suffering from one of the above-listed hematopoietic disorders. The IRF-1 mRNA level in the "second biological sample" provides a standard for comparison. As will be appreciated in the art, once the levels for intact IRF-1 mRNA, $\Delta 2$ IRF-1 mRNA and $\Delta 23$ IRF-1 mRNA have been determined for any such "healthy" individual, they can be used repeatedly as a standard. In other words, once the standard is known, it is not necessary to assay IRF-1 mRNA levels from a second biological sample each time a first biological sample is assayed for an acceleration of exon skipping. Instead, pre-existing standard values can be used if desired.

Total cellular RNA can be isolated from a biological sample using any suitable technique such as the guanidinium-thiocyanate method. Isolation can occur using the single-step method described in Chomczynski and Sacchi, *Anal. Biochem.* 162:156–159 (1987). IRF-1 mRNA levels are then assayed using any appropriate method, including S1 nuclease mapping, the polymerase chain reaction (PCR), reverse transcription in combination with the polymerase chain reaction (RT-PCR), and reverse transcription in combination with the ligase chain reaction (RT-LCR).

S1 mapping can be performed as described in Fujita et al., *Cell* 49:357–367 (1987). The sequence of a cDNA coding for human IRF-1 is known (Maruyama et al., *Nucleic Acids Res.* 17:3292 (1989)). Briefly, to prepare probe DNA for use in S1 mapping, the sense strand of human IRF-1 cDNA can be used as a template to synthesize labeled antisense DNA. The antisense DNA can then be digested using an appropriate restriction endonuclease to generate DNA probes of a desired length. For example, digestion with BamHI allows isolation of a DNA probe containing nucleotide residues 217 to 464, which is useful for visualizing protected bands corresponding to intact, $\Delta 2$, and $\Delta 23$ IRF-1 mRNA. Northern blot analysis can be performed as described in Harada et al., *Cell* 63:303–312 (1990).

Preferably, IRF-1 mRNA levels are assayed using the RT-PCR method described in Makino et al., *Technique* 2:295–301 (1990). Using this method, the radioactivities of the "amplicons" in the polyacrylamide gel bands are linearly related to the initial concentration of the target mRNA. Thus, the RT-PCR method is useful for assaying levels of intact, $\Delta 2$, and $\Delta 23$ IRF-1 mRNAs. Briefly, this method involves adding total RNA isolated from a biological sample in a reaction mixture containing a RT primer and appropriate buffer. After incubating for primer annealing, the mixture can be supplemented with a RT buffer, dNTPs, DTT, RNase inhibitor and reverse transcriptase. After incubation to achieve reverse transcription of the RNA, the RT products are then subject to PCR using labeled primers. Alternatively, rather than labelling the primers, a labeled dNTP can be included in the PCR reaction mixture. PCR amplification can be performed in a DNA thermal cycler according to conventional technique. After a suitable number of rounds to achieve amplification, the PCR reaction mixture is electrophoresed on a polyacrylamide gel. After drying the gel, the radioactivity of the appropriate bands (corresponding to amplified intact, $\Delta 2$, and $\Delta 23$ IRF-1 mRNA) is quantified using an imaging analyzer. RT and PCR reaction ingredients and conditions, reagent and gel concentrations, and labeling methods are well known in the art. Variations on the RT-PCR method will be apparent to the skilled artisan.

Any set of oligonucleotide primers which amplify exons 2 and 3 and at least part of exons 1 and 4 of the intact IRF-1 cDNA transcript is useful in the present invention. Such primers amplify all three species of IRF-1 mRNA (i.e., intact, $\Delta 2$, and , $\Delta 23$ IRF-1 mRNA) resulting in "amplicons" of different sizes for easy visualization by gel electrophoresis. The relative amount of each amplicon provides information concerning whether the sample exhibits an acceleration of exon skipping in IRF-1 mRNA. Preferred primers for the PCR reaction include:

5'TTCCCTCTTCCACTCGGAGT3' (SEQ ID NO: 1) or

5'GATATCTGGCAGGGAGTTCA3' (SEQ ID NO: 2).

A preferred primer for the reverse transcription reaction is:

5'CTCTGGTCTTTCACCTCCTC3' (SEQ ID NO: 3).

Of course, primers based on the above but varying in either base sequence or nucleotide length can also be used provided that the stability of the duplex formed with the target nucleotide sequence is such that the primers perform their intended function.

Having generally described the invention, the same will be more readily understood through reference to the following example which is provided by way illustration and is not intended to be limiting.

EXAMPLE

Materials and Methods

RNA Isolation, S1 Mapping Analysis, and RNA Blotting Analysis

Total cellular RNA was isolated by the guanidinium-thiocyanate method. S1 mapping analysis was performed as previously described (Fujita et at., *Cell* 49:357–367 (1987)). To prepare probe DNA, pBluescript II SK(+) phage DNA containing the sense strand of the human IRF-1 cDNA FspI-KpnI fragment was used as template to synthesize $^{32}$P-labeled antisense DNA. The product was then digested by BamHI and probe DNA containing from nucleotide residue 217 to 464 (Maruyama et at., *Nucleic Acids Res.* 17:3292 (1989)) was isolated. The procedure for RNA blotting analysis is described in Harada et al., *Cell* 63:303–312 (1990). To prepare probe DNA, a 2.0 kb BamHI-PvuII fragment of IHa-204 (Miyamoto et al., *Cell* 54:903–913 (1988)) for β-actin was labeled by the random primer method (Amersham).

Synthetic Primers

The primers were designed to amplify the cDNA specifically. The primers of the human IRF-1 gene (Maruyama et at., *Nucleic Aids Res.* 17:3292 (1989)) were: the antisense primer for reverse transcription (RT), nucleotide (nt) 490 to 471; the sense primer for PCR, nt 92 to 111; the antisense primer for PCR, nt 470 to 451. The primers of IRF-2 gene (Itoh et al., *Nucleic Acids Res.* 17:8372 (1989)) were: the antisense primer for RT, nt 391 to 372; the sense primer for PCR, nt 19 to 38; the antisense primer for PCR, nt 367 to 348. The primers of β-actin gene (Ponte et al., *Nucleic Acids Res.* 12:1687–1696 (1984)) were: the antisense primer for RT, nt 470 to 451; the sense primer for PCR, nt 311 to 330; the antisense primer for PCR, nt 448 to 429. The primers of the mouse IRF-1 gene (Miyamoto et al., *Cell* 54:903–913 (1988)) were: the antisense primer for RT, nt 498 to 479; the sense primer for PCR, nt 105 to 124; the antisense primer for PCR, nt 478 to 459.

RT-PCR Analysis

The RT-PCR analysis was performed basically as previously described (Makino et al., *Technique* 2:295–301 (1990)). High specific labeling and fewer cycles of amplification are thought to provide higher sensitivity and clearer results, since the amplicons can be quantitatively detected at a stage where the PCR reaction follows first-order exponential kinetics (Wang et al., *Proc. Natl. Acad. Sci. USA* 86:9717–9721 (1989); Makino et al., *Technique* 2:295–301 (1990); Foley et at., *Trans. Genet.* 9:380–386 (1993)). In this assay, IRF-1, IRF-2 and β-actin cDNAs from the same RNA samples were subjected to PCR amplification, and the β-actin amplicon was used as a reference for mRNA quantitation (Makino et al., *Technique* 2:295–301 (1990)).

Total RNA was isolated by the single-step method described in Chomczynski and Sacchi, *Anal. Biochem.* 162:156–159 (1987). Five hundred nanograms of total RNA were added in a reaction mixture containing 1 pmol RT primer, 3.8 ml of 5×RT buffer (250 mM Tris-HCl [pH 8.3], 376 mM KCl, 15 mM MgCl$_2$) in a volume of 12.5 ml. The mixture was heated at 95° C. for 2 min., chilled on ice, and incubated at 37° C. for 30 min. After the annealing reaction, the mixture was supplemented with 0.2 ml of 5×RT buffer, 2 ml of 0.1M DTT, 4.0 ml of 2.5 mM each of dNTPs, 20U of RNase inhibitor (Takara), and 100U of Moloney murine leukemia virus (M-MLV) reverse transcriptase (GIBCO BRL) to a volume of 20 ml, then incubated at 37° C. for 60 min. The RT reaction products were then incubated at 90° C. for 5 min, chilled on ice, and added with 40 ml of distilled water. The PCR reaction was performed in a reaction mixture containing 10 mM Tris-HCl (pH 8.3), 50 mM KCl, 1.5 mM MgCl$_2$, 0.01% (w/v) gelatin, 200 ml of dNTPs, 1 mM each 5' and 3' $^{32}$P-end-labeled PCR primers, 0.25 U Taq DNA polymerase (Perkin-Elmer Cetus), and 3 ml of the RT reaction product in a volume of 10 ml. The amplification was performed with the Perkin-Elmer Cetus DNA thermal cycler as follows: 95° C. for 30 sec, 55° C. for 30 sec, 72° C. for 1 min. The cycles of reaction were determined in the exponential phase of amplification; 24 cycles for IRF-1 and IRF-2, 18 cycles for β-actin. One microliter of each PCR reaction mixture was electrophoresed in 5% polyacrylamide gel in 0.5×TBE buffer. The gels were dried and the radioactivity of the appropriate bands were quantified by the Fujix Bas 2000 imaging analyzer. The amount of IRF-1 and IRF-2 specific amplicons was normalized to the amount of β-actin amplicon from the same sample. These numbers were further normalized with respect to the levels of IRF-1 and IRF-2 amplicons (arbitrarily set to 1.00) found in NBM. 1 cells from a healthy donor. In the case of IRF-1 amplicons, multiple different mRNA species can be quantitated with the same primers as described in Wang et al., *Proc. Natl. Acad. Sci. USA* 86:9717–9721 (1989).

Construction of Plasmids

The above RT-PCR products each containing intact or alternative forms of IRF-1 cDNA were subcloned into pCRT™II (Invitrogen). For construction of the plasmids using in vitro transcription (pBH1, pBH1Δ2, and pBH1Δ23), the following DNA fragments were ligated; (i) EcoRI-BamHI backbone fragment from pBluescript II SK(+) (ii) EcoRI-EcoRV fragment from the pCRT™II derivatives containing IRF-1 cDNA (iii) EcoRV-BamHI fragment from pHIRF31 (Maruyama et al., *Nucleic Acids Res.* 17:3292 (1989)). The IRF-1 expression vectors under control of the actin promoter (pAct-H 1, pAct-H 1Δ2, and pAct-H1Δ23) were constructed by replacing HindIII-BamHI backbone fragment of the pBluescript derivatives with HindIII-BamHI backbone fragment of pAct-C (Harada et al., *Cell* 63:303–312 (1990)).

In Vitro Transcription and Translation

Capped synthetic mRNA was transcribed in the presence of cap analog and ribonucleotide triphosphate by T7 RNA polymerase with the T7 promoter of each derivative of pBluescript II containing the intact or mutant IRF-1 cDNAs (pBH1, pBH1Δ2, or pBH1Δ23). The reaction was performed as the manufacturer's protocol (Stratagene). The RNA was extracted with phenolchloroform and ethanol precipitated. The RNA was redissolved in water, and 0.8 mg of the RNA was added in vitro translation, using rabbit reticulocyte lysate (Amersham) at 30° C. for 60 min.

Gel Shift Assay

The assay was performed essentially as previously described (Harada et al., *Cell* 63:303–312 (1990)). $^{32}$P-labeled C 1 oligomer (containing two IRF binding motifs; Tanaka et al., *Mol. Cell. Biol.* 13:4531–4538 (1993)) was used as probe DNA.

DNA Transfection and CAT Assay

P19 embryonal carcinoma cells (2.5×10$^5$ cells/5 cm dish) were transfected with 5 mg of p-55C1B reporter gene, which contains four IRF binding motifs (Fujita et al., *Cell* 49:357–367 (1987); Tanaka et al., *Mol. Cell. Biol.* 13:4531–4538 (1993)), and 5 mg of the IRF-1 expression vector. CAT assay was carried out as described (Harada et al., *Cell* 63:303–312 (1990)).

Colony-Forming Assay in Methylcellulose Gel

The IRF-1$^{-/-}$ embryonic fibroblast cells expressing an activated form of c-Ha-ras, rasEF11 (5×10$^5$ cells/10 cm dish), were co-transfected with 15 mg of the IRF-1 expression vector and 0.3 mg of the pMiwhph (Kato et al., *Mol. Cell. Biol.* 10:486–491 (1990)) by the calcium phosphate method (Harada et al., *Cell* 63:303–312 (1990)). Seventy-two hours after the transfection, cells were suspended with 1.3% methylcellulose gel dissolved in culture medium containing 200 mg/ml hygromycin and overlayed on an agarose bed composed of 0.53% agarose and culture medium. Colonies were scored 3 weeks after plating.

Results

Exon skipping in the human IRF-1 gene

Figure 1:
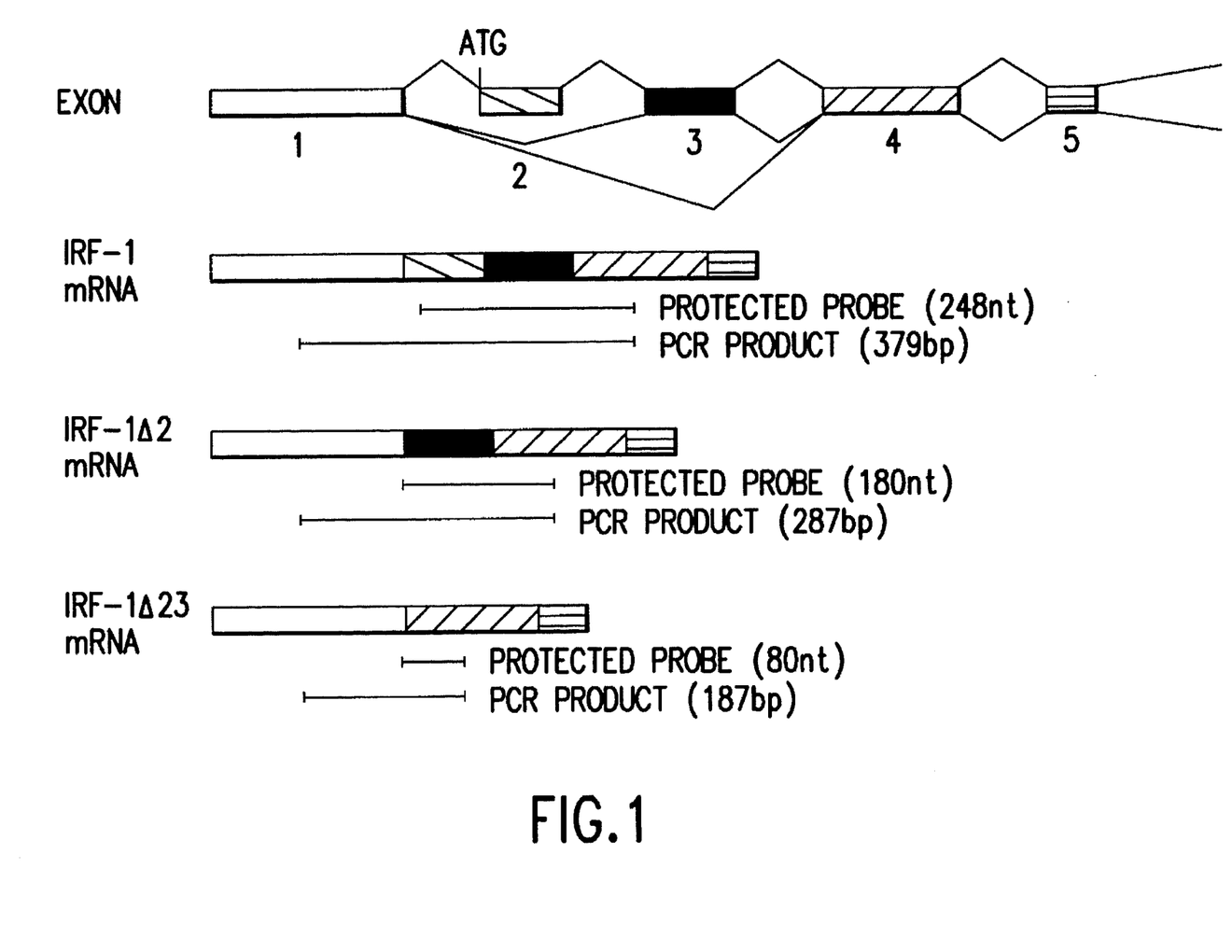
FIG. 1: The alternative splicing of human IRF-1 pre-mRNA. In the top panel exons are numbered as indicated, and lines connecting the exons represent splicing. The initiator ATG sequence within exon 2 is indicated. In the lower panel the intact and the alternative splicing forms of IRF-1 mRNA are shown. The expected sizes of the probes protected from S1 digestion and the products of RT-PCR amplification are indicated.
Figure 2:
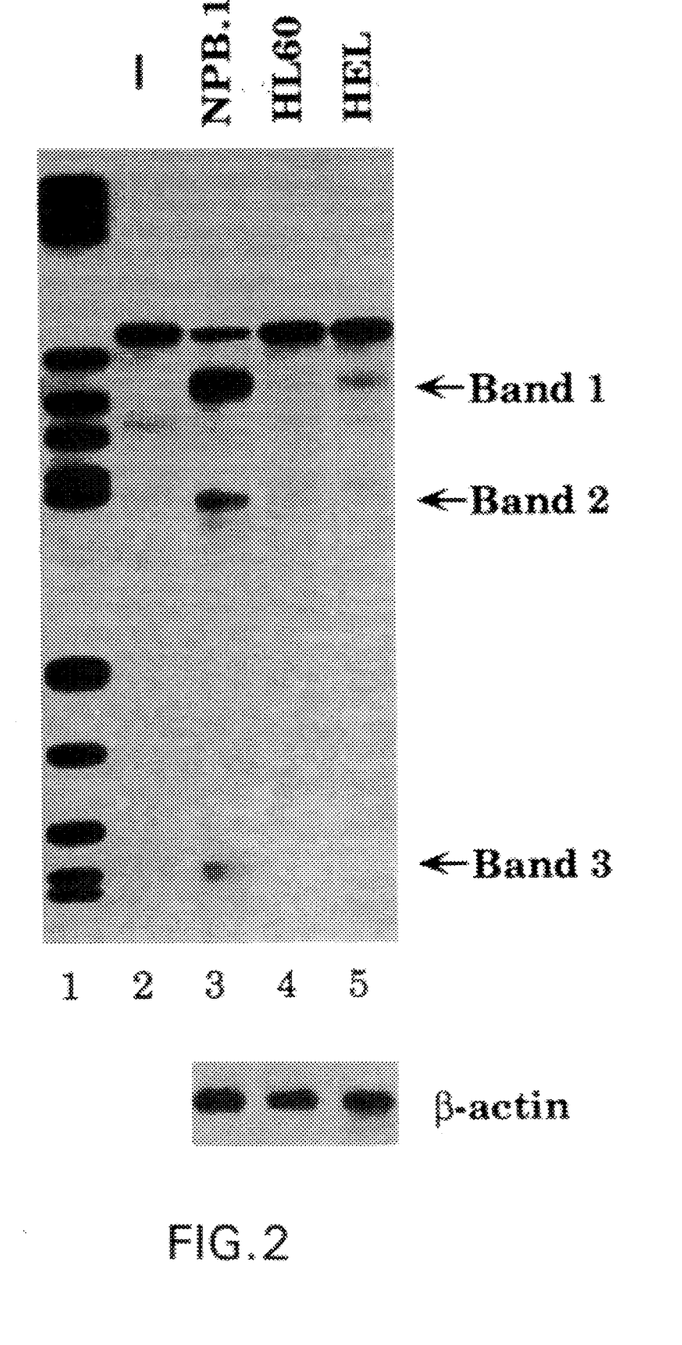
FIG. 2: Detection of the alternative splicing forms of IRF-1 prem-RNA by S1 mapping analysis. Total RNA was isolated from peripheral blood mononuclear (PBM) cells of a healthy volunteer (NPB. 1), HL-60 cells, and HEL cells. Upper panel; 15 mg of the RNAs were subjected to S1 mapping analysis (see Experimental Procedures). Lane 1, $^{32}$P-labeled HaeIII-digested pBR322 DNA fragments; lane 2, yeast tRNA as a negative control; lane 3, PBM cells from a healthy donor (NPB. 1); lane 4, HL-60; lane 5, HEL. The arrows indicate the positions of protected probes as described in FIG. 1. Lower panel; 2.5 mg of the RNAs were subjected to Northern blot analysis and the filter was hybridized with a β-actin probe.
Figure 3:
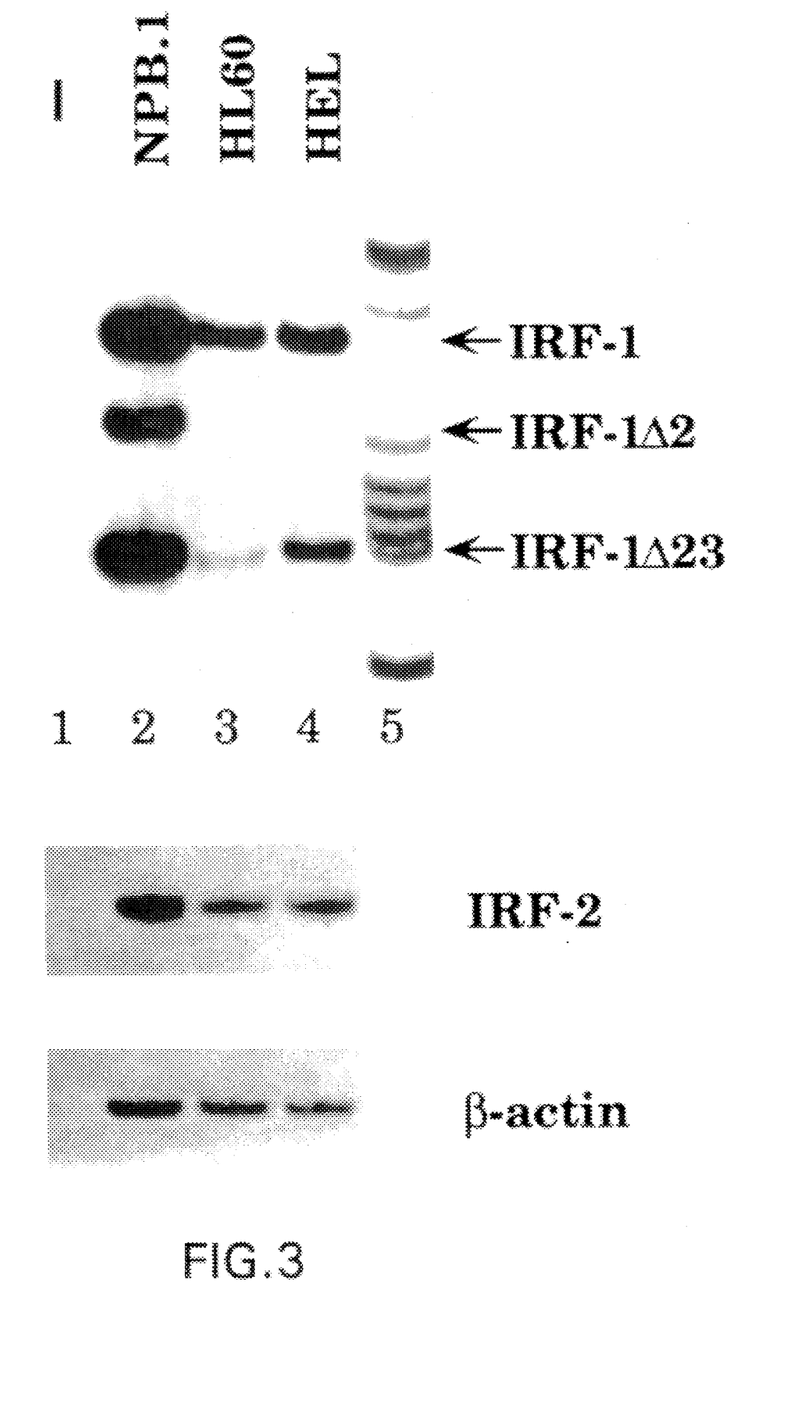
FIG. 3: RT-PCR analysis of IRF-1, IRF-2, and β-actin mRNA in PBM cells from a healthy donor, HL-60, and HEL. Five hundred nanograms of total RNA were reverse-transcribed into cDNA using primers specific for IRF-1, IRF-2 and β-actin, respectively. The cDNA product was subjected to PCR with labeled primers (see Experimental Procedures). Lane 1, yeast tRNA as a negative control; lane 2, PBM cells from a healthy donor (NPB. 1); lane 3, HL-60; lane 4, HEL; lane 5, $^{32}$P-labeled HaeIII-digested pBR322 DNA fragments. In the upper panel, the arrows indicate the positions of PCR products as described in FIG. 1. In the middle and lower panel the IRF-2 and β-actin specific amplicons, respectively, are shown.
Figure 4:
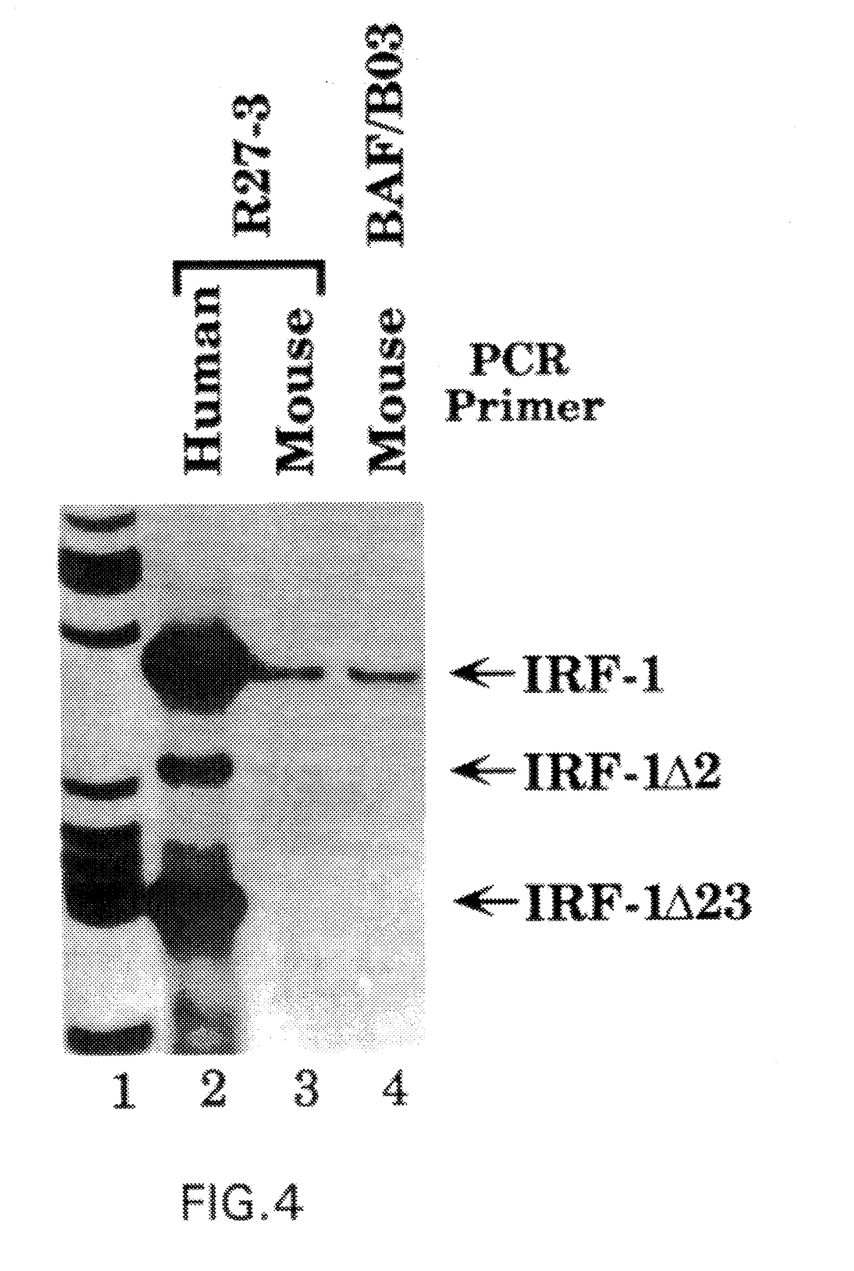
FIG. 4: RT-PCR analysis of the human versus murine IRF-1 mRNAs. Total RNAs from an NIH 3T3-derived clone transfected with the human IRF-1 genomic DNA (R27-3; Harada et al., Science 259:971–974 (1993)) and from mouse BAF/B03 were subjected to RT-PCR analysis using human or mouse IRF-1 specific primers (see Experimental procedures). The arrows indicate the positions of PCR products as described in FIG. 1. Lane 1, $^{32}$P-labeled HaeIII-digested pBR322 DNA fragments; lane 2, human IRF-1 amplicons in NIH 3T3-derived clone (R27-3); lane 3, mouse IRF-1 amplicon in R27-3; lane 4, mouse IRF-1 amplicons in BAF/B03.

The human IRF-1 gene consists of 10 exons, with the initiator ATG sequence located within the second exon (FIG. 1; Cha et al., *DNA Cell Biol.* 11:605–611 (1993); Harada et al., *Mol. Cell. Biol.* 14:1500–1509 (1994)). During an analysis of IRF-1 mRNA expression in various cell lines by S1 mapping, we noted the expression of unusual transcripts. As shown in FIG. 2, three protected bands were detected using total RNA from the peripheral blood mononuclear (PBM) cells of a healthy donor.[1] The upper band (Band 1; 248 nucleotides) corresponds to the intact IRF-1 mRNA. Judging by their size, the other two bands may correspond to RNAs lacking exon 2 (Band 2; 180 nucleotides), and exons 2 and 3 (Band 3; 80 nucleotides), respectively. However, these results were somewhat obscure in two hematopoietic cell lines, HL-60 and HEL, due to low mRNA expression levels. In the case of HL-60, this may be explained by the lack of one IRF-1 allele, since the cell has lost one chromosome 5 (Gallagher et at., *Blood* 54:713–733 (1979)). In order to achieve a more quantitative and qualitative analysis of these RNAs, we next performed a polymerase chain reaction (PCR) assay. In this assay, reverse transcription of mRNA was followed by PCR amplification (RT-PCR), in which the PCR products (amplicons) were labeled to high specific activity (see Experimental Procedures for the details). As shown in FIG. 3, three bands were again detected with the RNA from PBM cells, diagnostic for the Bands 1, 2 and 3 which were generated by the S1 mapping analysis (FIG. 1). Nucleotide sequence analysis of the PCR-amplified cDNAs revealed that the upper, middle and lower bands in fact correspond to intact IRF-1 mRNA, IRF-1 mRNA lacking exon 2 (Δ2mRNA), and IRF-1 mRNA lacking exons 2 and 3 (Δ23mRNA), respectively (results not shown). The Δ2 and Δ23 mRNAs are also expressed in HL-60 and HEL cells. In addition, a mouse NIH 3T3-derived cell line R27-3 (Harada et al., *Science* 259:971–974 (1993)), which contains a transfected 19 kb human IRF-1 gene, also showed the same pattern of exon skipping, indicating that this exon skipping occurs independent of the host cell type and chromosomal location. In contrast, when similar RT-PCR analysis was performed for the mouse IRF-1 mRNA using mouse specific primers, only a single band representing the intact mRNA was amplified in R27-3 and mouse hematopoietic cell line BAF/B03 (FIG. 4). Thus, the observed exon skipping may be an intrinsic property of the human IRF-1 gene. Importantly, the loss of exon 2 in the Δ2 and Δ23 mRNAs should result in the lack of the genuine initiator AUG sequence (FIG. 1, Harada et al., *Mol. Cell. Biol.* 14:1500–1509 (1994)) (see below).

[1] Another 9 samples from healthy donors were examined, and they all essentially showed expression pattern similar to that observed in this case.

Acceleration of IRF-1 mRNA exon skipping in MDS/leukemia

Figure 5:
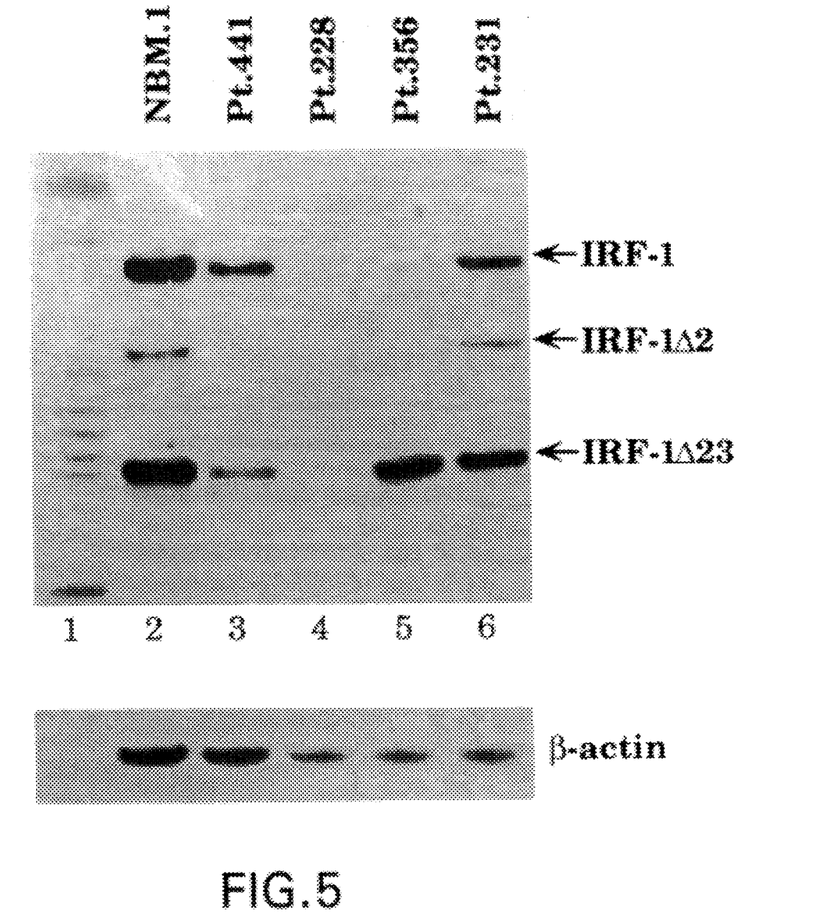
FIG. 5: RT-PCR analysis of mRNA from representative MDS/leukemia patients. RT-PCR was performed with total RNAs from a healthy donor and from MDS/leukemia patients (see Experimental Procedures). In the upper panel the arrows indicate the positions of the PCR products as described in FIG. 1. Lane 1, $^{32}$P-labeled HaeIII-digested pBR322 DNA fragments; lane 2, bone marrow cells from a healthy donor (NBM. 1); lane 3, Pt.441; lane 4, Pt.228; lane 5, Pt.356; lane 6, Pt.231. In the lower panel, β-actin specific amplicons are shown.

It has been shown that IRF-1 functions as a tumor suppressor (Harada et al., *Science* 259:971–974 (1993)) and deletion and/or rearrangement of either one or both of the IRF-1 alleles may be critical for the development of human MDS and leukemias (Willman et al., *Science* 259:968–971 (1993)). On the other hand, only a certain proportion of these hematopoietic disorders are accompanied by the 5q anomaly (Kerim et al., *Leukemia* 4:12–16 (1990); Pedersen-Bjergaard et al., *Blood* 76:1083–1091 (1990); Willman et al., *Science* 259:968–971 (1993)). The above findings prompted us to examine the status of exon skipping in cells from patients with MDS or leukemias secondary to MDS. Total RNA was isolated from either bone marrow (BM) cells or PBM cells and subjected to the RT-PCR assay. The results of some typical examples are shown in FIG. 5. A striking difference is obvious between the BM cells from the healthy donor and those from MDS/leukemia patients. In fact, the amplicon representing the intact IRF-1 mRNA is barely detectable in two of the samples presented here (Pts. 228 and 356), whereas the amplicon for Δ23 mRNA is still detectable. In contrast, the amount of β-actin mRNA specific amplicon remained relatively constant (see Experimental Procedure and Table 1).

We performed a similar analysis for a total of 25 RNA samples from patients with MDS or leukemias secondary to MDS, and the results are summarized in Table 1. The amounts of the IRF specific amplicons were first quantitatively determined by image analysis (Fujix Bas 2000) and then normalized to the amount of β-actin amplicon from the same sample; the expression of the β-actin mRNA is relatively invariant among the sample RNAs (Makino et al., *Technique* 2:295–301 (1990); Foley et al., *Trans. Genet.* 9:380–386 (1993)). These numbers were further normalized with respect to the levels of IRF-1 and IRF-2 amplicons (arbitrarily set to 1.00) found in NBM.1 cells from a healthy donor. Thus, the number appearing in Table 1 represent the expression of the intact, Δ2, Δ23 IRF-1 mRNAs and IRF-2 mRNA relative to those of a healthy donor, although they do not provide information regarding absolute mRNA copy number.

Notably, the amplicon representing intact IRF-1 mRNA was not detected in RNA samples from Pts. 581 and 117 cells, neither of which showed cytogenetic aberrations in the 5q region (Table 1).[2] In addition, another 5 samples (Pts. 190, 356, 228, 255, 578) gave very low levels of the intact amplicons, whereas the Δ2 and Δ23 amplicons, particularly the Δ23 amplicon, were still detectable. Six out of these patient samples were also analyzed for p53 mutations by RT-PCR/SSCP analysis, and all except one (Pt. 356) showed no evidence for such mutation (Table 1; Sugimoto et al., *Blood* 81:3022–3025 (1993)). Although not as profound as observed in the above samples, several other samples (e.g. Pts. 570, 716, 194, 199, 707) also show noticeably lower levels of the intact IRF-1 mRNA amplicons. We also analyzed RNA from patients with different types of hematopoietic malignancies, and found little or no intact IRF-1 amplicon in some of these samples, including 2 out of 4 AML patients who expressed only the Δ23 mRNA (results not shown). It may be worth noting that some RNA samples showed elevated levels of the IRF-2 specific amplicon (e.g. Pts. 581, 199, 534, 715).

[2] Thus far, RT-PCR/SSCP analysis of four patients with MDS or leukemia which showed an acceleration of exon skipping (Pts. 255, 356, 707 and 716) did not reveal any DNA deletions or mutations within IRF-1 exon sequences, nor did DNA sequencing reveal any alteration of intron sequences known to affect splicing. In addition, Southern blotting analysis of the DNAs of these patients showed no sign of gross rearrangements of the IRF-1 gene (results not shown).

Analysis of the Δ2 and Δ23 mRNA products

Figure 6:
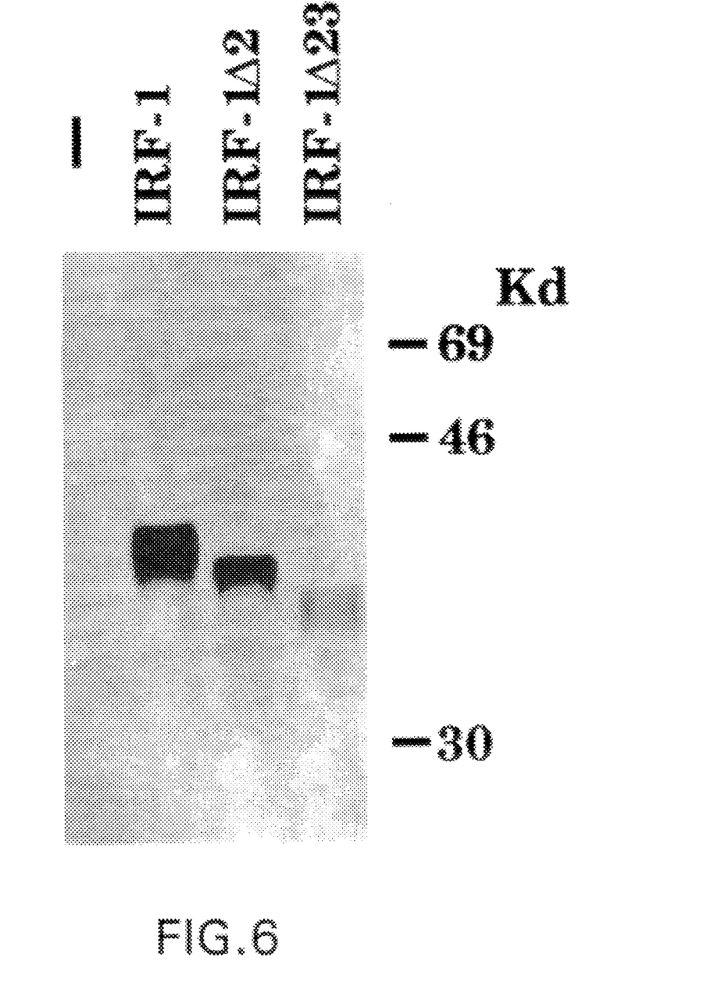
FIG. 6: In vitro translated products of the intact and alternative forms of IRF-1. One microliter of each translation reaction (10 ml) was analyzed on a 12.6% SDS-polyacrylamide gel.
Figure 7:
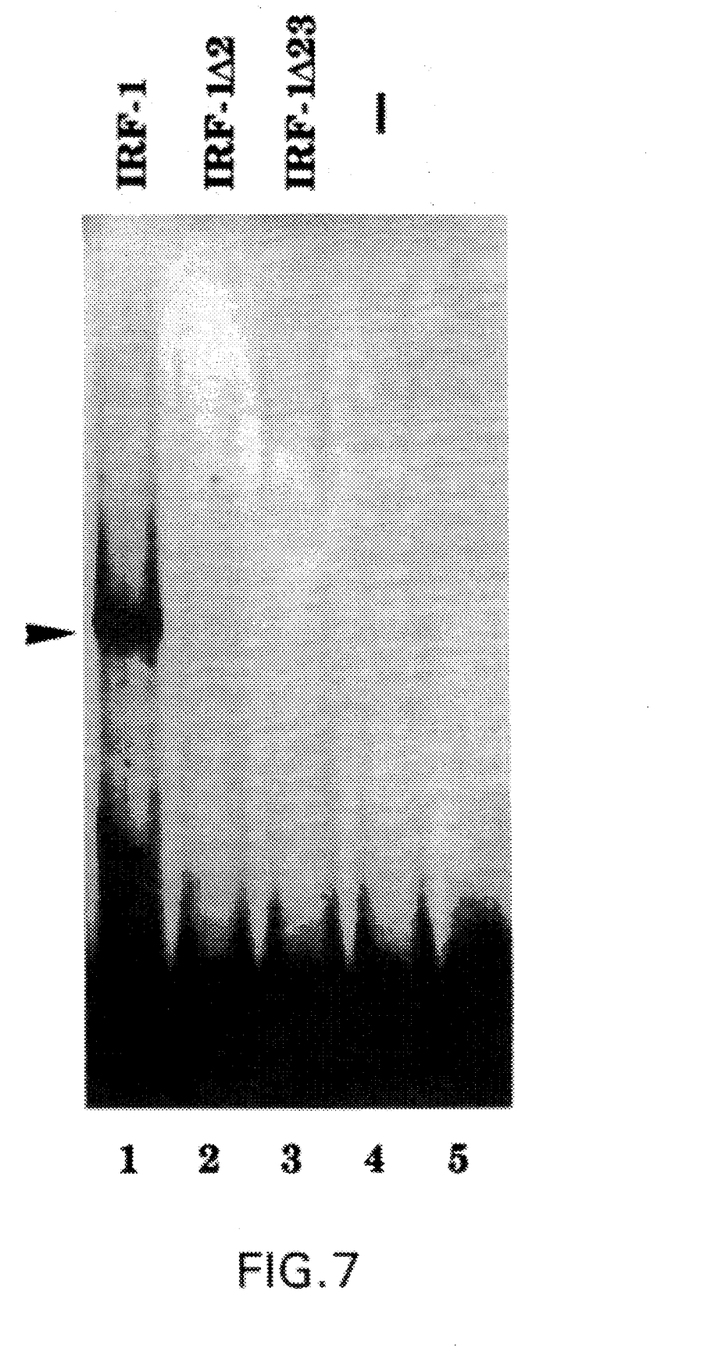
FIG. 7: The DNA binding activity of the IRF-1 mutants. The in vitro translated proteins shown in FIG. 6 were subjected to gel shift assay. Lane 4, in vitro translated product without RNA; lane 5, no extract. The arrowhead indicates the position of the IRF-1-DNA complex.
Figure 8:
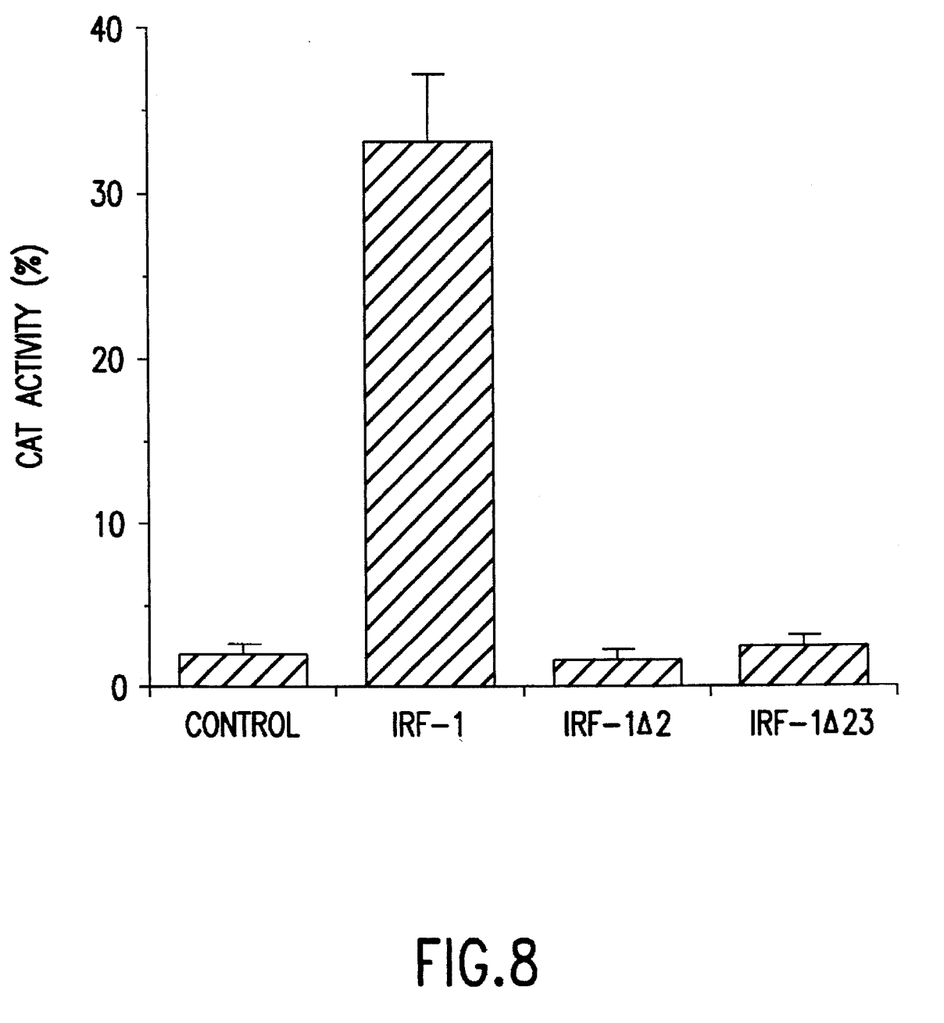
FIG. 8: Transcriptional activation by the IRF-1 mutants. P19 cells were transfected with 5 mg of the CAT reporter gene p-55C1B and 5 mg of the effector genes. The transfected effector genes were as follows: control, 5 mg of pAct-C; IRF-1, 2.5 mg of pAct-H1 and 2.5 mg of pAct-C; IRF-1Δ2, 2.5 mg of pAct-H1Δ2 and 2.5 mg of pAct-C; IRF-1Δ23, 2.5 mg of pAct-H1Δ23 and 2.5 mg of pAct-C. The transfection was duplicated and the assay was repeated three times; results were essentially reproducible.

Although both the Δ2 and Δ23 mRNAs lack the genuine initiation codon for IRF-1, these mRNAs may still direct synthesis of new proteins. cDNAs were constructed which correspond to the Δ2 or Δ23 mRNAs, and used to direct an in vitro transcription-translation reaction. When the $^{35}$S methionine-labeled products were analyzed by SDS-PAGE, distinct bands were detected for the wild type, the Δ2 and Δ23 cDNAs (FIG. 6). The size of the Δ2 and Δ23 cDNA products, termed IRF-1Δ2 and IRF-1Δ23, may correspond to truncated IRF-1 proteins whose synthesis had initiated at the AUG codons 32 (in exon 3) and 85 (in exon 4), respectively. As shown in FIG. 7, gel shift assay revealed that both IRF-1Δ2 and IRF-1Δ23 fail to bind to an oligomer containing two high-affinity IRF-Es (C1 oligomer; Tanaka et al., *Mol. Cell. Biol.* 13:4531-4538 (1993)). Co-transfection of each cDNA into a IRF-negative cell line (P19; Harada et al., *Cell* 63:303-312 (1990)) along with a reporter plasmid containing IRF-Es in its promoter showed that the protein encoded by the intact IRF-1 cDNA, but not those encoded by Δ2 or Δ23 cDNAs, could activate the reporter (FIG. 8). Co-transfection of the Δ2 or Δ23 cDNAs with the intact IRF-1 cDNA did not affect IRF-1-mediated gene activation, suggesting that neither IRF-1Δ2 nor IRF-1Δ23 acts in a dominant-negative manner on IRF-1-mediated transcriptional activation (results not shown).

The intact human IRF-1 but not IRF-1Δ23 shows tumor suppressor activity

In most of the samples in which expression of intact IRF-1 mRNA is low or undetectable, the Δ23 mRNA is nevertheless expressed at relatively high levels (Table 1). We therefore addressed the issue of whether the IRF1Δ23 manifests tumor suppressor activity. IRF-1$^{-/-}$ EFs expressing an activated form of c-Ha-ras oncogene were transfected with expression vectors containing the cDNA encoding either intact IRF-1 or IRF-1Δ23, together with the hygromycin (hgr) resistance gene (pMiwhph; Kato et at., *Mol. Cell. Biol.* 10:486-491 (1990)). The transfectants were plated on methylcellulose gel, and the number of hgr-resistant colonies was subsequently counted. As shown in Table 2, transfection of the cDNA for IRF-1 resulted in a profound inhibition of colony formation, whereas no such effect was seen with the cDNA for IRF-1Δ23. These results indicate that IRF-1Δ23 lacks of tumor suppressor activity, presumably as the result of the loss of its DNA binding activity.

TABLE 1

The expression of intact and alternative-spliced forms of IRF-1 in cells from MDS/leukemia patients

| | Source | Age, Sex | % Blasts[a] | p53mut.[b] | Karyotype[c] | IRF-1 | IRF-1Δ2 | IRF-1Δ23 | IRF-2[d] |
|---|---|---|---|---|---|---|---|---|---|
| (NORMAL BM) | | | | | | | | | |
| NBM.1 | BM | 38,M | N.D. | N.D. | N.D. | 1.00 | 0.16 | 0.83 | 1.00 |
| NBM.2 | BM | 65,M | N.D. | N.D. | N.D. | 0.97 | 0.07 | 0.46 | 0.76 |
| (RA) | | | | | | | | | |
| Pt. 190 | BM | 38,F | 5.0% | (−) | N.D. | 0.05 | 0.05 | 2.36 | 1.31 |
| Pt. 356 | BM | 74,M | 4.0% | (+) | 46, XY, −18, 5q−, 9q−, +mar | 0.08 | 0.12 | 1.31 | 0.91 |
| Pt. 441 | BM | 43,M | 4.0% | (−) | 46, XY, 12p−, 20q−, 21p+/46, XY, 12p−, 20q−, 21p+, 21p+ | 0.42 | 0.03 | 0.19 | 1.40 |
| Pt. 581 | BM | 65,M | 4.9% | (−) | 46, Xq−, Y, 8q+ | 0.00 | 0.00 | 0.15 | 3.24 |
| Pt. 585 | BM | 45,F | 0.8% | (−) | 46, XX | 0.43 | 0.07 | 0.32 | 2.68 |
| (RAEB) | | | | | | | | | |
| Pt. 535 | BM | 54,M | 12.4% | (−) | 46, XY | 0.89 | 0.16 | 0.73 | 1.26 |
| Pt. 570 | BM | 61,M | 8.1% | (+) | 47, XY, −5, −7, −12, −18, +22, 15p+, +4mar | 0.39 | 0.06 | 0.29 | 1.73 |
| (RAEB-t) | | | | | | | | | |
| Pt. 228 | BM | 72,M | 30.0% | (−) | 46, XY | 0.08 | 0.02 | 0.20 | 0.73 |
| (CMMoL) | | | | | | | | | |
| Pt. 255 | BM | 34,M | 5.8% | N.D | 46, XY, 5q−, 8p+, 13q+, 20q+ | 0.09 | 0.64 | 5.39 | 2.49 |
| Pt. 492 | PB | 57,M | 9.0% | N.D | 46, XY | 1.03 | 0.01 | 0.32 | 2.36 |
| Pt. 519 | BM | 28,M | 0.5% | N.D | 46, XY | 0.86 | 0.19 | 0.75 | 0.75 |
| Pt. 711 | PB | 77,F | 0.0% | N.D | N.D. | 0.93 | 0.15 | 0.53 | 2.23 |
| Pt. 716 | BM | 52,M | 5.7% | N.D | 46, XY, 3q+, 5p−q−, 10p+, 13q− | 0.37 | 0.01 | 0.46 | 2.59 |
| (MDS/LEU) | | | | | | | | | |
| Pt. 117 | PB | 42,M | ~100.0% | (−) | 45, X, −Y | 0.00 | 0.00 | 7.80 | 1.89 |
| Pt. 194 | BM | 68,M | 43.6% | N.D. | 46, XY/44, XY, −2, −5, −7, −9, −10, −17, −18, −20, 19p+, +6mar | 0.37 | 0.15 | 0.52 | 0.49 |
| Pt. 199 | BM | 60,F | 68.0% | (−) | 46, XX | 0.30 | 0.33 | 4.01 | 6.51 |
| Pt. 231 | BM | 55,M | 77.6% | N.D. | 46, XY | 0.77 | 0.14 | 1.19 | 1.20 |
| Pt. 447 | BM | 44,F | 67.0% | (−) | 46, XX, t(11;19) | 1.00 | 0.48 | 1.06 | 1.69 |
| Pt. 534 | BM | 60,F | 50.0% | (−) | 46, XX | 0.63 | 0.13 | 0.38 | 3.76 |
| Pt. 543 | BM | 44,F | 35.3% | (−) | 46, XX, t(11;19) | 1.19 | 0.08 | 0.38 | 2.77 |
| Pt. 578 | BM | 55,F | 71.6% | (−) | 46, XX, 7p−, 11q+ | 0.15 | 0.00 | 0.15 | 1.83 |
| Pt. 706 | PB | 44,M | 30.0% | N.D. | 46, XY | 0.75 | 0.03 | 0.47 | 2.94 |
| Pt. 707 | PB | 56,M | 50.0% | N.D. | 47, XY, +8 | 0.39 | 0.02 | 0.42 | 1.09 |
| Pt. 713 | BM | 57,M | 43.6% | N.D. | 44, X, −Y, −18, 5q− | 0.47 | 0.07 | 0.42 | 1.21 |
| Pt. 715 | BM | 64,M | 70.6% | N.D. | 46, XY | 0.67 | 0.04 | 0.21 | 3.21 |

TABLE 1-continued

The expression of intact and alternative-spliced forms of IRF-1 in cells from MDS/leukemia patients

| Source | Age, Sex | % Blasts[a] | p53mut.[b] | Karyotype[c] | IRF-1 | IRF-1Δ2 | IRF-1Δ23 | IRF-2[d] |
|---|---|---|---|---|---|---|---|---|
| (Cell Lines) | | | | | | | | |
| HL-60 | | | | | 0.34 | 0.03 | 0.08 | 0.44 |
| K 562 | | | | | 1.01 | 0.03 | 0.29 | 1.91 |
| HEL | | | | | 0.55 | 0.04 | 0.20 | 0.90 |
| Hela | | | | | 0.51 | 0.17 | 0.49 | 0.81 |
| GM637 | | | | | 0.29 | 0.12 | 0.22 | 0.81 |

RA, refractory anemia;
RAEB, refractory anemia with excess of blasts;
RAEB–t, RAEB in transformation;
CMMoL, chronic myelomonocytic leukemia;
MDS/LEU., overt leukemia from myelodysplastic syndrome;
BM, bone marrow;
PB, peripheral blood;
F, female;
M, male;
N.D., not done;
p53mut., mutation of p53.
[a]Determined by morphological criteria using FAB classification.
[b](−): no mutations were detected. (+): mutations were detected. Mutations of the p53 gene in MDS/leukemia patients were determined by RT–PCR/SSCP analysis as described in Sugimoto et al., Blood 81:3022–3026 (1993).
[c]Representative metaphase chromosome spreads were karyotyped according to the International System for Human Cytogenetic Nomenclature (ISCN, 1991).
[d]The IRF–1 and IRF–2 values were normalized relative to the β–actin signal. The values of IRF–1 intact form and IRF–2, respectively, of the representative normal bone marrow NBM.1 were assigned the value of 1.00. Each value is a mean of triplicate assays.

TABLE 2

Supression of colony-forming ability by the intact or an alternative splicing form of IRF-1

| Transfected Construct | Number of colonies | | |
|---|---|---|---|
| | Experiment 1 | Experiment 2 | Experiment 3 |
| pAct-C | 995 | 934 | 699 |
| pAct-H1 | 381 | 246 | 353 |
| pAct-H1Δ23 | 844 | 803 | 813 |

Transfected constructs are as follows:
pAct-C, control actin promoter vector;
pAct-H1, acting promoter expressing intact IRF-1 cDNA;
pAct-H1Δ23, actin promoter expressing IRF-1 cDNA lacking exons 2 and 3.

It will be appreciated to those skilled in the art that the invention can be performed within a wide range of equivalent parameters of composition, concentrations, modes of administration, and conditions without departing from the spirit or scope of the invention or any embodiment thereof.

The disclosures of all references, patent applications, and patents recited herein are hereby incorporated by reference.

What is claimed is:

1. A method for detecting an acceleration of exon skipping in interferon-regulatory factor-1 (IRF-1) mRNA, the method comprising:

(a) assaying IRF-1 mRNA level in a first biological sample, wherein said IRF-1. mRNA is selected from one or more of intact IRF-1 mRNA, Δ2 IRF-1 mRNA, or Δ23 IRF-1 mRNA;

(b) comparing said IRF-1 mRNA level to an IRF-1 mRNA standard level, said standard being taken from a second biological sample not exhibiting accelerated exon skipping in IRF-1 mRNA; and   (c) determining whether said sample exhibits an acceleration of exon skipping in IRF-1 mRNA.

2. The method of claim 1, wherein an acceleration of exon skipping is exhibited if the intact IRF-1 mRNA level in said first sample is lower relative to the intact IRF-1 mRNA level in said standard.

3. The method of claim 1, wherein an acceleration of exon skipping is exhibited if the ratio between the intact IRF-1 mRNA level and the Δ2 IRF-1 mRNA level or the Δ23 IRF-1 mRNA level in said first sample is lower relative to said ratio in said standard.

4. A method of assisting the diagnosis of a hematopoietic disorder, the method comprising:

(a) assaying IRF-1 mRNA level in a first biological sample obtained from an individual, wherein said IRF-1 mRNA is selected from one or more of intact IRF-1 mRNA, Δ2 IRF-1 mRNA, or Δ23 IRF-1 mRNA;

(b) comparing said IRF-1 mRNA level to an IRF-1 mRNA standard level, said standard being taken from a second biological sample riot exhibiting accelerated exon skipping in IRF-1 mRNA; and   (c) determining whether said sample exhibits an acceleration of exon skipping in IRF-1 mRNA, whereby an acceleration Of exon skipping in IRF-1 mRNA is indicative of a hematopoietic disorder.

5. The method of claim 4, wherein an acceleration of exon skipping is exhibited if the intact IRF-1 mRNA level in said first sample is lower relative to the intact IRF-1 mRNA level in said standard.

6. The method of claim 4, wherein an acceleration of exon skipping is exhibited if the ratio between the intact IRF-1 mRNA level and the Δ2 IRF-1 mRNA level or the Δ23 IRF-1 mRNA level in said first sample is lower relative to said ratio in said standard.

7. The method of claim 4, wherein said hematopoietic disorder is a myelodysplastic syndrome (MDS) selected from refractory anemia (RA), refractory anemia with ringed sideroblasts (RARS), refractory anemia with excess of blasts (RAEB), RAEB in transformation (RAEBT), or chronic myelomonocytic leukemia (CMML).

8. The method of claim 4, wherein said hematopoietic disorder is selected from acute myeloid leukemia (AML) or overt leukemia from myelodysplastic syndrome (MDS/Leu).

9. The method of claim 1, wherein said IRF-1 mRNA level is assayed by RT/PCR analysis.

10. The method of claim 4, wherein said IRF-1 mRNA level is assayed by RT/PCR analysis.

11. The method of claim 9, wherein at least one of the oligonucleotides
  5'TTCCCTCTTCCACTCGGAGT3' (SEQ ID NO: 1),
  5'GATATCTGGCAGGGAGTTCA3' (SEQ ID NO: 2), or
  5'CTCTGGTCTTTCACCTCCTC3' (SEQ ID NO: 3)
is used as a primer during said analysis.

12. The method of claim 10, wherein at least one of the oligonucleotides
  5'TTCCCTCTTCCACTCGGAGT3' (SEQ ID NO: 1),
  5'GATATCTGGCAGGGAGTTCA3' (SEQ ID NO: 2), or
  5'CTCTGGTCTTTCACCTCCTC3' (SEQ ID NO: 3)
is used as a primer during said analysis.

13. The method of claim 1, wherein said first biological sample is obtained from peripheral blood mononuclear cells (PBM) or bone marrow cells.

14. The method of claim 4, wherein said first biological sample is obtained from peripheral blood mononuclear cells (PBM) or bone marrow cells.

15. The method of claim 1, wherein said second biological sample is obtained from an individual not suffering from a hematopoietic disorder.

16. The method of claim 4, wherein said second biological sample is obtained from an individual not suffering from a hematopoietic disorder.

* * * * *

UNITED STATES PATENT AND TRADEMARK OFFICE
CERTIFICATE OF CORRECTION

PATENT NO. : 5,643,729

DATED : July 1, 1997

INVENTORS : Taniguchi *et al.*

It is certified that an error appears in the above-identified patent and that said Letters Patent is hereby corrected as shown below.

In column 15, line 35, change "IRF-1. mRNA" to "IRF-1 mRNA".

In column 15, line 62, change "riot" to "not"; and line 66, change "Of" to "of".

Signed and Sealed this

Nineteenth Day of May, 1998

Attest:

Attesting Officer

BRUCE LEHMAN

*Commissioner of Patents and Trademarks*

SEQUENCE LISTING ( 1 ) GENERAL INFORMATION:

( i i i ) NUMBER OF SEQUENCES: 3

( 2 ) INFORMATION FOR SEQ ID NO: 1:

( i ) SEQUENCE CHARACTERISTICS:
        ( A ) LENGTH: 20 base pairs
        ( B ) TYPE: nucleic acid
        ( C ) STRANDEDNESS: single
        ( D ) TOPOLOGY: linear     ( i i ) MOLECULE TYPE: cDNA     ( x i ) SEQUENCE DESCRIPTION: SEQ ID NO: 1:

```
TTCCCTCTTC CACTCGGAGT                                                          20
```

( 2 ) INFORMATION FOR SEQ ID NO: 2:

( i ) SEQUENCE CHARACTERISTICS:
        ( A ) LENGTH: 20 base pairs
        ( B ) TYPE: nucleic acid
        ( C ) STRANDEDNESS: single
        ( D ) TOPOLOGY: linear     ( i i ) MOLECULE TYPE: cDNA     ( x i ) SEQUENCE DESCRIPTION: SEQ ID NO: 2:

```
GATATCTGGC AGGGAGTTCA                                                          20
```

( 2 ) INFORMATION FOR SEQ ID NO: 3:

( i ) SEQUENCE CHARACTERISTICS:
        ( A ) LENGTH: 20 base pairs
        ( B ) TYPE: nucleic acid
        ( C ) STRANDEDNESS: single
        ( D ) TOPOLOGY: linear     ( i i ) MOLECULE TYPE: cDNA     ( x i ) SEQUENCE DESCRIPTION: SEQ ID NO: 3:

```
CTCTGGTCTT TCACCTCCTC                                                          20
```